(12) United States Patent
Hairault et al.

(10) Patent No.: US 7,901,948 B2
(45) Date of Patent: Mar. 8, 2011

(54) USE OF MOLECULAR TWEEZERS AS SENSITIVE MATERIALS IN CHEMICAL SENSORS FOR DETECTING OR ASSAYING ORGANIC COMPOUNDS IN THE VAPOUR STATE

(75) Inventors: Lionel Hairault, Blere (FR); Pierre Montmeat, La Riche (FR); Eric Pasquinet, Saint Avertin (FR); Jean-Michel Barbe, Bretigny (FR); Stéphane Brandes, Dijon (FR); Franck Denat, Dijon (FR); Claude Gros, Neuilly-les-Dijon (FR); Roger Guilard, Fontaine les Dijon (FR)

(73) Assignee: Commissariat A l'Energie Atomique, Paris (FR)

( * ) Notice: Subject to any disclaimer, the term of this patent is extended or adjusted under 35 U.S.C. 154(b) by 674 days.

(21) Appl. No.: 11/883,393

(22) PCT Filed: Feb. 1, 2006

(86) PCT No.: PCT/FR2006/050088
§ 371 (c)(1),
(2), (4) Date: Mar. 3, 2008

(87) PCT Pub. No.: WO2006/082343
PCT Pub. Date: Aug. 10, 2006

(65) Prior Publication Data
US 2008/0153168 A1    Jun. 26, 2008

(30) Foreign Application Priority Data
Feb. 2, 2005  (FR) .................... 05 50304

(51) Int. Cl.
*G01N 1/22*  (2006.01)
(52) U.S. Cl. ......... 436/181; 436/106; 436/119; 436/127; 436/172; 436/125; 436/140
(58) Field of Classification Search ............... 436/181, 436/106, 119, 127, 172, 125, 140
See application file for complete search history.

(56) References Cited

U.S. PATENT DOCUMENTS
2003/0027936 A1  2/2003  Murray et al.
(Continued)

FOREIGN PATENT DOCUMENTS
WO     WO 03/011865     2/2003
OTHER PUBLICATIONS

Sanchez-Pedreno, J.A.O., et al., "The investigation of coating materials for the detection of nirtobenzene with coated quartz piezoelectric crystals", Analytica Chimica Acta, 1986, p. 285-291, vol. 182.
(Continued)

*Primary Examiner* — Jill Warden
*Assistant Examiner* — M. Cole
(74) *Attorney, Agent, or Firm* — Brinks Hofer Gilson & Lione

(57) ABSTRACT

The invention relates to the use of molecular tweezers as sensitive materials in chemical sensors intended to detect or assay organic compounds in the vapour state, and in particular nitro compounds.
These molecular tweezers correspond to the general formula (I):

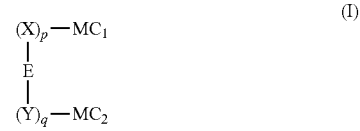

in which:
  $MC_1$ and $MC_2$ represent macrocycles;
  p and q are equal to 0 or 1;
  X and Y are optionally substituted $C_1$ to $C_{10}$ alkylene groups; while
  E represents an optionally substituted cyclic or heterocyclic spacer group;
and in which $MC_1$ and $MC_2$ are positioned facing each other. Fields of application: detection of explosives, control and monitoring of atmospheric pollution and of the quality of ambient air in relatively confined spaces, and monitoring of industrial sites.

20 Claims, 4 Drawing Sheets

U.S. PATENT DOCUMENTS

2004/0152826 A1 8/2004 Therien et al.
2006/0287195 A1 12/2006 Jerome et al.

OTHER PUBLICATIONS

Ali Umar, A., et al., "Self-assembled monolayer of copper(II) meso-tetra(4- sulfanatophenyl) porphyrin as an optical gas sensor" Sensors and Actuators B, Jun. 15, 2004, pp. 231-235, vol. 101, No. 1-2, Search Report.

Andersson, Marcus, et al.,"Development of a ChemFET sensor with molecular films of porphyrins as sensitive layer" Sensors and Actuators B, Jun. 15, 2001, pp. 567-571, vol. 77, No. 1-2, Search Report.

Barbe, Jean Michael, et al., "Metallocorroles as sensing components for gas sensors: remarkuable affinity and selectivity of cobalt(III) corroles for CO vs O2 and $N_2$." Dalton Trans. Mar. 23, 2004, pp. 1208-1214, Search Report.

Baron, M.G., et al., "Luminescent porphyrin thin films for NOX sensing" Sensors and Actuators B, 1993, pp. 195-199, No. 11, Search Report.

Beletskaya, Irina P., et al., "Synthesis of 1,8-bis(cyclam) and 1,8-bis(azacrown) substituted anthracenes by palladium-catalyzed arylation of cyclam" Tetrahedron Letters, Feb. 11, 2002, pp. 1193-1196, vol. 43, No. 7, Search Report.

Kadish, K.M., et al., "Synthesis, physicochemical and electrochemical properties of metal-metal bonded ruthenium corrole homodimers" Journal of Organometallic Chemistry, Jun. 1, 2002, pp. 69-76, vol. 652, No. 1-2, Search Report.

Bolze, F. et al., "Fine tuning of the photophysical properties of cofacial diporphyrins via the use of different spacers" Journal of Organometallic Chemistry, Feb. 1, 2002, pp. 89-97, vol. 643-644, Search Report.

Brandes, S., et al., "New Synthesis of Cylindrical Macroticyclic Ligand in Tetraazamacrocycle Series", Comptes Rendus de l Academie des Sciences, Jun. 3, 1996, pp. 827- 833, vol. 322, No. 11, Search Report.

Brandes, Stephane et al., "Synthesis of Macropolycyclic Ligands based on Tetraazacycloalkanes." Eur. J. Org. Chem, 1998, pp. 2349-2360, Search Report.

Di Natale, C., et al., "Characterization and design of porphyrins-based broad selectivity chemical sensors for electronic nose applications" Sensors and Actuators B, Sep. 15, 1998, pp. 162-168, vol. 52, No. 1-2, Search Report.

Kurosawa, Shigeru et al., "Gas Sorption to Plasma-Polymerized Copper Phthalocyanine Film Formed on a Piezoelectric Crystal." Analytical Chemistry, Feb. 15, 1990, pp. 353-359, vol. 62, No. 4, Search Report.

Faure, Sebastien et al., "Role of the Spacer in the Singlet-Singlet Energy Transfer Mechanism in Cofacial Bisporphyrins" J. Am. Chem. Soc., Jun. 1, 2004, pp. 1253-1261, vol. 126, No. 4, Search Report.

Lachkar, Mohammed et al, "Synthesis of New Binucleating Cylindrical Macrotricyclic Ligands Where Two Cyclam Rings are an a Face-To-Face Conformation. Characterization of Their Dicopper(II) and Dinickel(II) Complexes" Inorganic Chemistry, Mar. 13, 1998, pp. 1575-1584, vol. 37, No. 7, Search Report.

Pacholska, Ewa, et al., "New Route to a Face to Face Biscorrole Free-Base and the Corresponding Heterobimetallic Copper (III)-Silver(III) Complex" Dalton Transactions, Sep. 16, 2004, pp. 3181-3183, Search Report.

Spadavecchia, J. et al., "Spin-Coated Thin Films of Metal Porphyrin-Phthalocyanine Blend for an Optochemical Sensor of Alcohol Vapours" Sensors and Actuators B, Jun. 1, 2004, pp. 88-93, vol. 100, No. 1-2, Search Report.

Tredgold, R.H. et al., "Gas Sensors Made from Langmuir-Blodgett Films of Porphyrins" IEE Proceedings, Jun. 1, 1985, pp. 151-156, vol. 132, part 1, No. 3, Search Report.

USE OF MOLECULAR TWEEZERS AS SENSITIVE MATERIALS IN CHEMICAL SENSORS FOR DETECTING OR ASSAYING ORGANIC COMPOUNDS IN THE VAPOUR STATE

TECHNICAL FIELD

The present invention relates to the use of molecular tweezers as sensitive materials in chemical sensors intended to detect or assay organic compounds in the vapour state, and more specifically nitro compounds such as nitroaromatics (nitrobenzene, dinitrobenzene, trinitrobenzene, nitrotoluene, dinitrotoluene, trinitrotoluene, etc.), nitramines, nitrosamines and nitric esters.

Such sensors are especially useful for detecting explosives, whether for the purpose of ensuring security in public places such as airports, for checking the legality of merchandise in circulation in a territory, for combating terrorism, for carrying out disarmament operations, for locating antipersonnel mines or else for decontaminating industrial or military sites.

They are also useful for protecting the environment, in particular for the control and monitoring of atmospheric pollution and of the quality of ambient air in relatively confined spaces, and also for the monitoring, for security purposes, of industrial sites manufacturing, storing and/or handling nitro compounds.

PRIOR ART

The detection of explosives is a problem of vital interest, especially as regards civil security.

At the present time, several methods are used to detect the vapour of nitro compounds incorporated in the composition of explosives, such as the use of "sniffer" dogs trained for this purpose, laboratory analysis, for example by chromatography coupled to a mass spectrometer or to an electron capture detector for samples taken on site, or else infrared detection.

These methods generally prove to be very sensitive, which is essential for detecting explosives considering the very low vapour concentration of nitro compounds that exists in the vicinity of an explosive. However, they are not completely satisfactory.

Thus, the use of "sniffer" dogs has the drawback of requiring lengthy training of the dogs and their handlers and of being unsuitable for prolonged operations due to the fact that the attention span of dogs is limited.

As for the other methods, the sheer size of the apparatus that they use, their energy consumption and their operating costs oppose the development of detection systems that are easily transportable and autonomous and, consequently, capable of being used on any type of site.

In recent years, the development of sensors capable of detecting gaseous chemical species in real time has expanded rapidly. The operation of these sensors is based on the use of a film of a sensitive material, that is to say of a material having at least one physical property P (mass, temperature, electrical conductivity, absorbance, fluorescence, etc.) that is modified when in contact with the gaseous molecules sought, which covers a system capable of measuring, in real time, any variation of this physical property and of thus proving the presence of the gaseous molecules sought.

The advantageous of chemical sensors relative to the aforementioned methods are many: instant results, possibility of miniaturization and, therefore, portability, handleability and substantial autonomy, low manufacturing and operating costs, etc.

However, it is obvious that their performance is extremely variable, depending on the nature of the sensitive material used.

To date, a certain number of studies have been carried out that aim to research sensitive materials for the detection of gaseous nitro compounds, and more particularly nitroaromatic compounds. Thus, the possibility of using polysiloxanes, polyethylene glycols, carbon type adsorbents, cyclic organic compounds (copper phthalocyanin, cyclodextrins and cavitans) dendrimers and fluorescent compounds have been studied.

Furthermore, trapping compounds with "molecular tweezers", that is to say molecules composed of two, generally aromatic, branches joined to one another by a spacer group, was proposed at the end of the 1970s.

The possibility of trapping aromatic or nitroaromatic compounds in a liquid medium using different types of tweezers has since been demonstrated by a certain number of authors, but the latter were not interested in trapping these compounds in a gaseous medium.

Now, within the scope of their work on the development of chemical sensors intended more especially for detecting explosives, the inventors have found that face-to-face bismacrocycle type molecular tweezers react with very high sensitivity in the presence of vapours of nitro compounds, and more generally vapours of organic compounds, and are therefore likely to form sensitive materials of choice for detecting or assaying these compounds when they are in the vapour state.

It is this observation that forms the basis of the invention.

SUMMARY OF THE INVENTION

The subject of the invention is therefore the use of at least one compound corresponding to the general formula (I) below:

in which:
  $MC_1$ and $MC_2$, which may be identical or different, represent macrocycles;
  p and q, which may be identical or different, are equal to 0 or 1;
  X and Y, which may be identical or different, are optionally substituted alkylene groups comprising from 1 to 10 carbon atoms; while
  E represents an optionally substituted cyclic or heterocyclic spacer group;
and in which $MC_1$ and $MC_2$ are positioned facing each other; as a sensitive material in a chemical sensor for detecting or assaying an organic compound in the vapour state.

Within the context of the present invention, the term "macrocycle" is generally understood to mean an organic molecule that may be composed of a single ring or of several rings joined together, either directly by a simple bond, or via a bridging atom or group, and of which the ring or the set of rings comprises, preferably, from 8 to 60 carbon atoms and one or more heteroatoms, this molecule possibly being metalled, that is to say being linked to a metal atom, and/or substituted.

Furthermore, the expression "arranged facing each other" means that the macrocycles $MC_1$ and $MC_2$ are oriented in the compound so as to be opposite each other but that does not mean that these macrocycles are necessarily parallel to one another.

Thus, the macrocycles $MC_1$ and $MC_2$ may especially be chosen, independently of one another, from metalled and non-metalled, substituted and unsubstituted porphyrins, phthalocyanins, naphthalocyanins, sapphyrins, corroles, corrolazines and macrocyclic polyamines of the polyazamacrocycle or dioxopolyazamacrocycle type.

The metal to which the macrocycles $MC_1$ and/or $MC_2$ may be joined, when these macrocycles are metalled, may be a priori any element considered to be a metal in the meaning of the Periodic Table of the Elements, also known under the name Mendeleev's Periodic Table, namely an alkali metal such as lithium, an alkaline-earth metal such as magnesium, a transition metal such as iron, cobalt, zinc, copper, nickel, manganese, chromium or titanium, or else a metal from columns III, IV and V of this periodic table such as lead.

This metal may, in addition, be joined to a halogen atom or to a hydroxyl group, that is to say that it may be in the form of a metal halide or hydroxide.

The substituent or substituents borne by the macrocycles $MC_1$ and/or $MC_2$, when these are substituted, may be chosen from:
- linear, branched or cyclic, saturated or unsaturated hydrocarbon groups comprising from 1 to 100 carbon atoms and optionally having one or more heteroatoms and/or one or more chemical functional groups comprising at least one heteroatom and/or one or more aromatic or heteroaromatic groups;
- chemical functional groups comprising at least one heteroatom; and
- optionally substituted aromatic or heteroaromatic groups.

When this or these substituents consist of a hydrocarbon group and when this group comprises at least two carbon atoms and has one or more heteroatoms and/or one or more chemical functional groups comprising at least one heteroatom and/or one or more aromatic or heteroaromatic groups, then this or these heteroatoms, this or these chemical functional groups and this or these aromatic or heteroaromatic groups may either form a bridge inside this hydrocarbon group or be borne laterally by it or else be located at its end.

In what has gone before and what follows, the term "heteroatom" is understood to mean any atom other than carbon or hydrogen such as, for example, an oxygen, sulphur, nitrogen, fluorine, chlorine, phosphorus or else boron atom, oxygen, nitrogen, sulphur and halogen atoms being preferred.

The expression "chemical functional group comprising at least one heteroatom" is understood to mean any chemical functional group having one or more atoms other than carbon or hydrogen and, especially, a functional group having one or more oxygen, sulphur, nitrogen and/or halogen atoms. This chemical functional group may, in particular, be chosen from the following functional groups: —COOH, —COOR, —CHO, —CO, —OH, —OR, —SH, —SR, —$SO_2$R, —$NH_2$, —NHR, —NRR', —$CONH_2$, —CONHR, —CONRR', —C(Hal)$_3$, —OC(Hal)$_3$, —C(O)Hal, —CN, —COR, —COOCOR and phenol, in which:
- R represents a linear, branched or cyclic, saturated or unsaturated $C_1$ to $C_{100}$ hydrocarbon group, or else a simple bond in the case where said chemical functional group forms a bridge in a hydrocarbon group;
- R' represents a linear, branched or cyclic, saturated or unsaturated $C_1$ to $C_{100}$ hydrocarbon group, this group possibly being identical to or different from the hydrocarbon group represented by R; while
- Hal represents a halogen atom, for example a fluorine, chlorine or bromine atom.

The term "aromatic group" is understood to mean any hydrocarbon group composed of one or more unsaturated $C_3$ to $C_6$ rings and having conjugated double bonds, and the term "heteroaromatic group" is understood to mean any aromatic group such as has just been defined, but comprising one or more heteroatoms in the ring or in at least one of the rings that form it. As examples of aromatic groups likely to be used, mention may be made of cyclopentadienyl, phenyl, benzyl, biphenyl, phenylacetelenyl, pyrenyl or anthracenyl, while as examples of heteroaromatic groups, mention may be made of furanyl, pyrrolyl, thiophenyl, oxazolyl, pyrazolyl, thiazolyl, imidazolyl, triazolyl, pyridinyl, pyranyl, quinolinyl, pyrazinyl and pyrimidinyl.

When such an aromatic or heteroaromatic group is substituted, then it has, preferably, one or more chemical functional groups comprising at least one heteroatom such as those mentioned above.

The spacer group E may be, generally, any cyclic or heterocycle group; the inventors having, indeed, observed that regardless of the nature of the spacer group, the compounds of general formula (I) are capable of being used as sensitive materials in gravimetric sensors, that is to say sensors whose operation is based on a change in the mass of these materials.

Thus, this spacer group may be a saturated or unsaturated, even aromatic or heteroaromatic, monocyclic or polycyclic group. As examples of spacer groups, mention may be made of phenyl, pyrenyl, anthracenyl, naphthalenyl, dibenzofuranyl, biphenylenyl, dibenzothiophenyl, xanthenyl, metallocenyl, (for example, ferrocenyl), ortho-, meta- or para-xylenyl, carbazolyl, acridinyl, phenazinyl, phenoxazinyl, binaphthyl, phenothiazinyl, fluorenyl, diphenyl ether oxide and calix[n]arenyl groups where n is an integer ranging from 4 to 12.

However, it is also possible to play on the choice of spacer group to give the compounds of general formula (I) particular physical properties, which are capable of being modified in the presence of the compounds that it is desired to detect and that are easily measurable, making the compounds of general formula (I) able to also be used as sensitive materials in sensors other than gravimetric sensors.

Thus, for example, a spacer group having fluorescent properties such as an anthracenyl, xanthenyl or else acridinyl group, makes it possible to produce a fluorescence sensor, whereas a spacer group of the dibenzothiophenyl type makes it possible to produce a resistive sensor, that is to say a sensor whose operation is based on a variation in the electrical conductivity of the sensitive material.

As previously indicated, when they are present, the alkylene groups X and Y may be substituted.

It is the same for the spacer group E.

According to the invention, the substituent or substituents capable of being borne by X, Y and/or E may be chosen from:
- linear, branched or cyclic, saturated or unsaturated, $C_1$ to $C_{30}$ hydrocarbon groups, optionally having one or more heteroatoms and/or one or more chemical functional groups comprising one or more heteroatoms and/or one or more substituted or unsubstituted aromatic or heteroaromatic groups;
- chemical functional groups having at least one heteroatom; and
- substituted or unsubstituted aromatic or heteroaromatic groups.

Here too, when this or these substituents consist of a hydrocarbon group and when this group comprises at least two carbon atoms and has one or more heteroatoms and/or one or more chemical functional groups and/or one or more aromatic or heteroaromatic groups, then this or these heteroatoms, this or these chemical functional groups and this or these aromatic or heteroaromatic groups may either form a bridge inside this hydrocarbon group or be borne laterally by it or else be located at its end.

Among the compounds used according to the invention, those corresponding to the general formula (I) are especially preferred, in which formula:

$MC_1$ and $MC_2$, which may be identical or different, represent two porphyrins or two phthalocyanins or two naphthalocyanins or two sapphyrins or two corroles or two corrolazines or two macrocyclic polyamines which are metalled or non-metalled, substituted or unsubstituted;

p and q are identical, X and Y are identical;

while E has the same meaning as before.

More specifically, those which correspond to the general formula (I) are preferred, in which formula:

$MC_1$ and $MC_2$ represent:

either two porphyrins chosen from those corresponding to formulae (II) and (III) below:

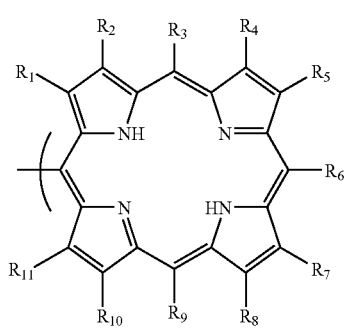
(II)

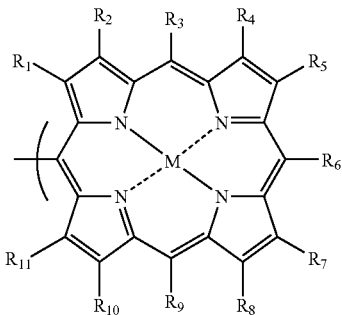
(III)

or two dioxopolyazamacrocycles chosen from those corresponding to formulae (IV) and (V) below:

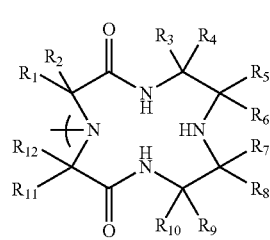
(IV)

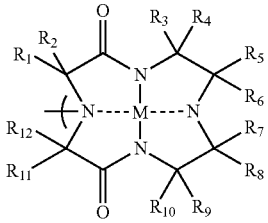
(V)

or two polyazamacrocycles chosen from those corresponding to formulae (VI) and (VII) below:

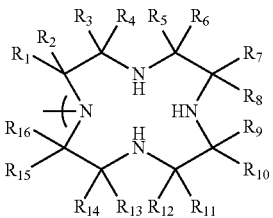
(VI)

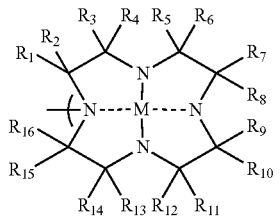
(VII)

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$, being identical or different, represent a hydrogen atom or a linear or branched, saturated or unsaturated, $C_1$ to $C_{10}$ hydrocarbon group and M represents a metal chosen from lithium, magnesium, iron, cobalt, zinc, copper, nickel, manganese, chromium, titanium and lead;

p and q are identical, X and Y are identical;

while E has the same meaning as before.

Such compounds are, for example:

bisporphyrins of particular formulae (IIIa), (IIIb) and (IIIc) below:

(IIIa)

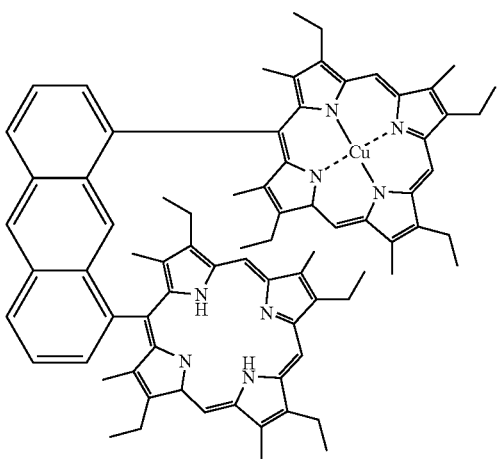

(IIIb)

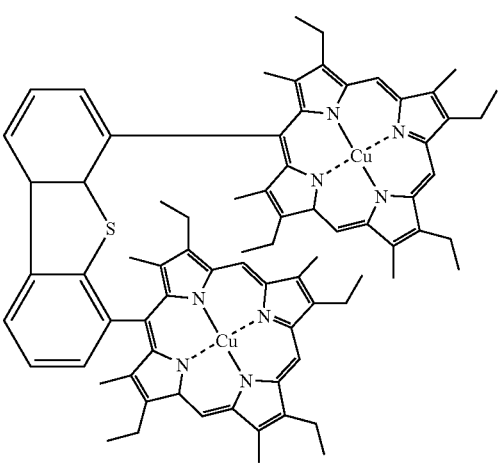

(IIIc)

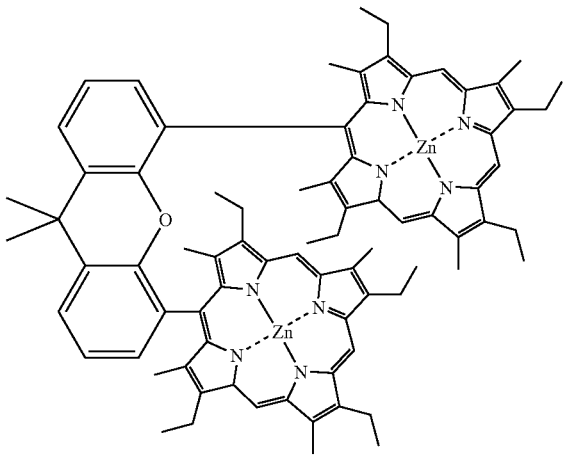

bispolyazamacrocycle of particular formula (IVa) below:

(IVa)

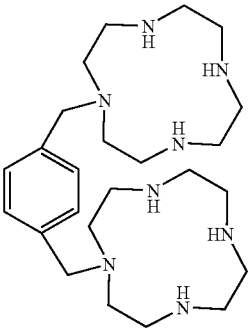

bisdioxopolyazamacrocycle of particular formula (VIa) below:

(VIa)

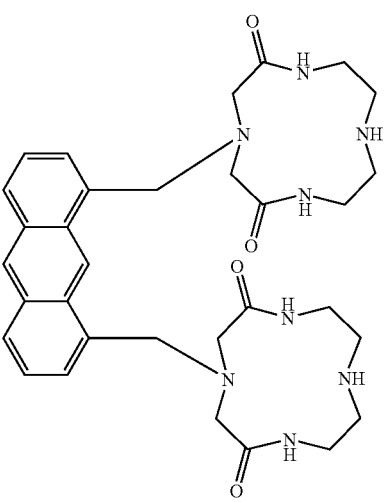

The compounds of general formula (I) may be synthesized by processes described in the literature.

In particular, the non-metalled bisporphyrins may be obtained by condensation of 4 free α-pyrol units on a group of formula (VIII) below:

(VIII)

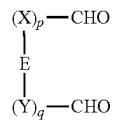

in which X, Y, p, q and E have the same meaning as before and the two —CHO groups are arranged facing each other, this condensation being carried out in ethanol under reflux in the presence of a catalytic amount of hydrochloric acid, which make it possible to obtain bis(dipyrrylmethanes) bearing 4 ethylester functional groups at the α-pyrrol positions. These esters are then hydrolysed with an alkaline solution, for example diethylene glycol at 100° C., then the temperature of the reaction medium is gradually raised to 190° C. to induce a gentle decarboxylation of the previously obtained but not separated tetra acids. Then, the free bis(α-tetra pyrryl-methanes) are subjected to a cyclization with a dipyrryl-methane (at a ratio of two molecules of dipyrrylmethane per molecule of bispyrrylmethane), in the presence of para-toluenesulphonic acid, followed by an oxidation with ortho-chloranil. The separation of the resulting bisporphyrins and their purification by column chromatography is facilitated due to a metallation by zinc that is then followed by a demetallation by a treatment in acid medium.

The dihomo-metalled bisporphyrins of the type of those corresponding to the particular formulae (IIIb) and (IIIc) may be obtained by subjecting the corresponding non-metalled bisporphyrins to a dimetallation, for example under reflux with a dichloromethane/methanol mixture and in the presence of an excess of the metal salt intended to be complexed, for example in the metal acetate form.

The mono-metalled bisporphyrins of the type of that corresponding to the particular formula (IIIa) may be obtained by subjecting the corresponding non-metalled bisporphyrins to two successive monometallations, the first with a metal intended to be used as a protective group for the porphyrin that it is desired not to metal, for example zinc in the form of zinc acetate, the second with the metal intended to be complexed by the other porphyrin, then by removing the first metal via a treatment in acid medium.

The dihetero-metalled bisporphyrins may be obtained in a similar manner to the bisporphyrins, apart from the fact that the first metal is not removed.

The bispolyazamacrocycles of the type of that corresponding to the particular formula (IVa) may be obtained by condensation of the corresponding tetraazacycloalkanes that are tri-protected by protecting groups, for example tert-butyloxycarbonyl (t-Boc), on a group:
either of formula (IX) below:

in which X, Y, p, q and E have the same meaning as before and the two —COCl groups are arranged facing each other, in which case this condensation is carried out in tetrahydrofuran in the presence of triethylamine, for 1 hour at room temperature then, after hydrolysis of the reaction medium and extracting with chloroform, the crude reaction mixture is chromatographed on silica gel to result in the intermediate bisamides;
or of formula (X) below:

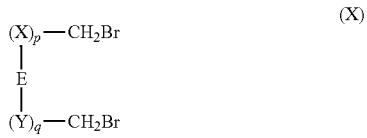

in which X, Y, p, q and E have the same meaning as before and the two —CH$_2$Br groups are arranged facing each other, in which the condensation is carried out under acetonitrile reflux in the presence of potassium carbonate for 48 hours, then, after evaporating the solvent, and chromatography on silica, the intermediate bisamides are obtained.

In both cases, the intermediate bisamides are reduced by an excess of borane in tetrahydrofuran and the t-Boc protecting groups are removed by acid hydrolysis with hydrochloric acid.

The bisdioxopolyazamacrocycles of the type of that corresponding to the particular formula (VIa) may, themselves, be obtained by a similar process to that which has just been described but starting from the corresponding dioxopolyazamacrocycles of which one amine functional group is protected by a t-Boc group.

According to the invention, the compound of general formula (I) is present in the sensor preferably in the form of a thin film that covers one or both sides of a substrate suitably chosen depending on the physical property of which the variations are intended to be measured by this sensor.

As a variant, the compound of general formula (I) may also be present in the sensor in the form of a solid object such as, for example, a cylinder having a certain porosity so as to make all the molecules of the compound of general formula (I) accessible to the compounds that it is desired to detect.

When the latter is present in the form of a thin film, this film has, preferably, a thickness of 10 angstroms to 100 microns.

Such a film may especially be obtained by spray coating, spin coating, drop coating or else by sublimation coating, all these coating techniques being well known to a person skilled in the art.

The substrate and the measurement system of the sensor are chosen depending on the physical property of the compound of general formula (I) of which the changes induced by the presence of the compounds to be detected are intended to be measured by the sensor.

In this particular case, the changes in mass of the compounds of general formula (I) and the changes in fluorescence of these compounds, when they have fluorescence properties, have proved to be particularly advantageous to measure.

Thus, the sensor is preferably a gravimetric sensor or a fluorescence sensor.

As examples of gravimetric sensors, mention may be made of quartz microbalance sensors, SAW (Surface Acoustic Wave) sensors, such as Love wave sensors and Lamb wave sensors, and also microlevers.

Among the gravimetric sensors, quartz microbalance sensors are more particularly preferred. This type of sensor, the operating principle of which has been described by J. A. O, Sanchez-Pedrono et al. in *Anal. Chem. Acta*, vol. 182, 1986, 285, schematically comprises a piezoelectric substrate (or resonator), generally a quartz crystal covered on both faces with a metal layer, for example made of gold or platinum, which is used as an electrode. As the sensitive material covers one or both faces of the substrate, any change in the mass of this material brings about a change in the vibration frequency of the substrate.

Obviously, it is also possible to use a compound of general formula (I) as a sensitive material in sensors designed to measure changes in a physical property other than mass and fluorescence such as, for example, resistive sensors based on the measurement of changes in the electrical conductivity or optical sensors based on the measurement of absorbance changes in the UV-visible range or else wavelength changes in the infrared range.

Furthermore, it is also possible to combine within one and the same device or "multisensor", several individual sensors comprising sensitive materials that are different from one another, or equipped with substrates and measurement systems that are different from one another such as, for example, one or more gravimetric sensors and/or one or more fluorescence sensors, the main thing being that at least one of the sensors comprises a compound of general formula (I).

Sensors comprising a compound of general formula (I) as a sensitive material have proved suitable for detecting or assaying, with a very high sensitivity, many organic compounds in the vapour state.

These organic compounds are especially nitro compounds, the presence of which they are capable of detecting at concentrations of the order of ppm (parts per million), even ppb (parts per billion), or even, in certain cases, ppt (parts per trillion), and in particular nitroaromatic compounds, nitramines, nitrosamines and nitric esters.

As examples of nitroaromatic compounds, mention may be made of nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene or else trinitrophenol (or picric acid).

Nitramines are, themselves, for example cyclotetramethylenetetranitramine (or octogen), cyclotrimethylenetrinitramine (or hexogen), and trinitrophenylmethylnitramine (or tetryl), whereas nitrosamines are, for example, nitrosodimethylamine.

As for the nitric esters, they are, for example, pentrite, ethylene glycol dinitrate, diethylene glycol dinitrate, nitroglycerine or nitroguanidine.

However, the organic compounds capable of being detected or assayed by the sensors are also volatile organic compounds, and in particular ketones, alcohols, chlorinated solvents and toluene type aromatic compounds.

Besides the abovementioned advantages, sensors having a compound of general formula (I) as sensitive material have also proved to have other advantages such as:

a rapid response and reproducibility of this response;
a performance stability over time and, consequently, a very satisfactory lifetime;
an ability to operate continuously;
a manufacturing cost that is compatible with a mass production of sensors, a very small amount of compound of general formula (I) (that is to say, in practice a few mg) being necessary for manufacturing a sensor; and
the possibility of being miniaturized and, consequently, of being able to be easily transported and handled on any type of site.

They are particularly useful for detecting explosives, especially in public places.

The invention will be better understood in the light of the remainder of the description, which relates to examples of the use of various examples of compounds useful according to the invention, in the form of thin films, as sensitive materials in quartz microbalance sensors and in fluorescence sensors.

Obviously, these examples are only given by way of illustrating the subject of the invention and do not constitute in any case a limitation of this subject.

DETAILED SUMMARY OF PARTICULAR EMBODIMENTS

EXAMPLE 1

Detection of a Nitro Compound (DNTFMB) by a Quartz Microbalance Sensor

In this example, a quartz microbalance sensor was used that comprised an AT cut quartz having a vibration frequency of 9 MHz, covered with two circular gold measurement electrodes (QA9RA-50 model, Ametek Precision Instruments), which had, on both of its faces, a thin film of bisporphyrin of particular formula (IIIa) represented above.

This film was deposited by sublimation of the bisporphyrin at a temperature of 100° C. and under a partial vacuum of $4\times10^{-5}$ mbar, until a 10 kHz change in the quartz vibration frequency was obtained.

The sensor was exposed successively to:
air for 7 minutes;
DNTFMB at a concentration of 3 ppm in air for 10 minutes; and
air for 20 minutes,
the air and the DNTFMB being at room temperature (25° C.).

Figure 1:
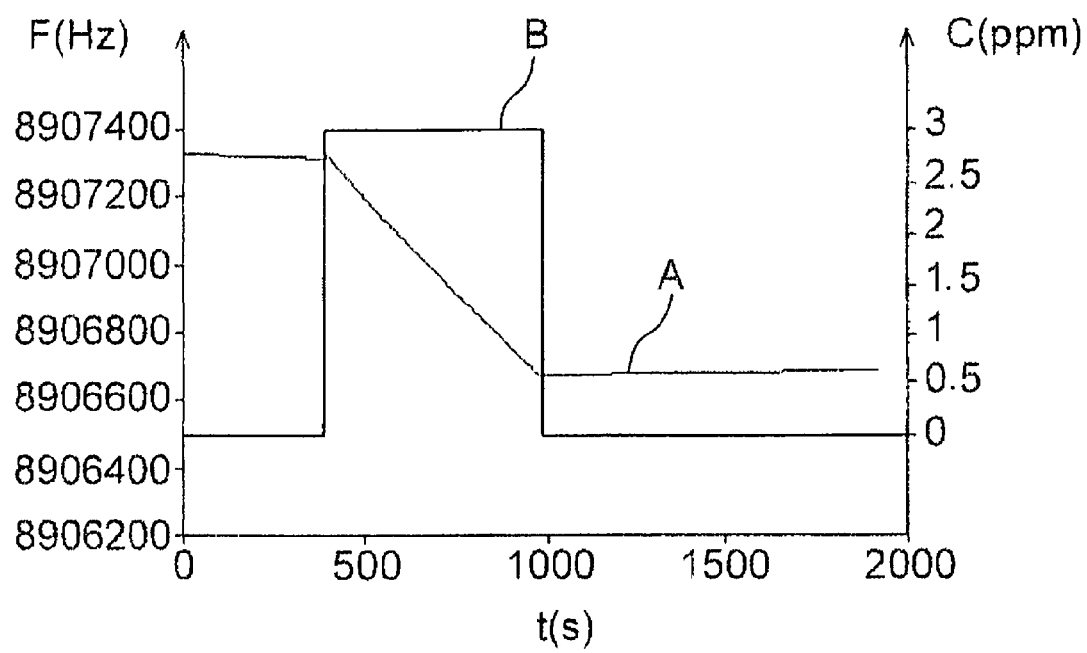
FIG. 1 shows the variation of the quartz vibration frequency of a quartz microbalance sensor comprising a thin film of a first example of a compound used according to the invention, when this sensor is exposed successively to air and to vapours of 2,4-dinitrotrifluoromethoxybenzene (DNTFMB).

FIG. 1 illustrates the variation of the quartz vibration frequency during these exposures. In this figure, the curve A represents the vibration frequency (F) of the quartz, expressed in hertz (Hz) as a function of the time (t) expressed in seconds (s), while the curve (B) represents the concentration of DNTFMB (C), expressed in ppm, also as a function of time.

EXAMPLE 2

Detection of Various Types of Organic Compounds by a Quartz Microbalance Sensor

In this example, a quartz microbalance sensor was used that comprised an identical quartz to that of the sensor used in Example 1, but of which the quartz was covered on both of its faces by a thin film of the bisporphyrin of particular formula (IIIb) represented above.

This film was deposited by sublimation of the bisporphyrin at a temperature of 100° C. and under a partial vacuum of $2\times10^{-5}$ mbar, until a 10 kHz change in the quartz vibration frequency was obtained.

The sensor was exposed successively to:
air for 8 minutes;
DNTFMB at a concentration of 3 ppm in air for 10 minutes;
air for 50 minutes;
DNTFMB at a concentration of 3 ppm in air for 10 minutes;
air for 130 minutes;
dichloromethane at a concentration of 580 000 ppm in air for 10 minutes;
air for 3 minutes;
methyl ethyl ketone at a concentration of 126 000 ppm in air for 10 minutes;
air for 6 minutes;
toluene at a concentration of 38 000 ppm in air for 10 minutes;
air for 8 minutes;
ethanol at a concentration of 79 000 ppm in air for 10 minutes; and
air for 2 minutes,
the air, DNTFMB, dichloromethane, methyl ethyl ketone, toluene and ethanol being at room temperature (25° C.).

Figure 2:
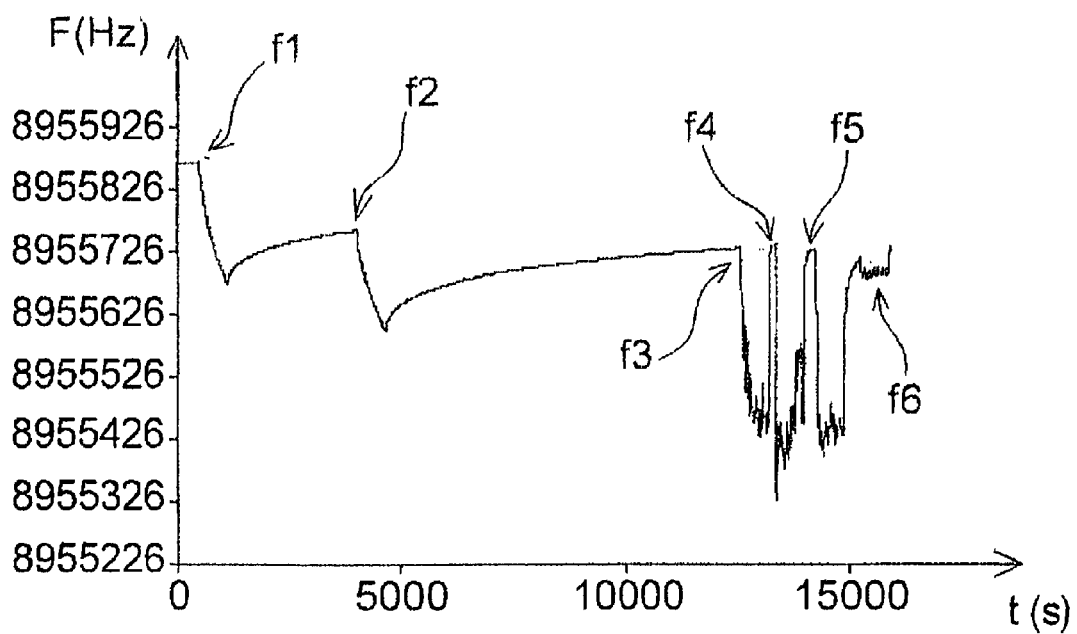
FIG. 2 shows the variation of the quartz vibration frequency of a quartz microbalance sensor comprising a thin film of a second example of a compound used according to the invention, when this sensor is exposed successively to air and vapours of DNTFMB, dichloromethane, methyl ethyl ketone, toluene and ethanol.

FIG. 2 illustrates the variation of the quartz vibration frequency during these exposures, in the form of a curve representing the vibration frequency (F) of the quartz, expressed in hertz (Hz), as a function of time (t), expressed in seconds (s), the arrows f1 and f2 marking the two exposures to DNTFMB, the arrow f3 marking exposure to dichloromethane, the arrow f4 marking the exposure to methyl ethyl ketone, the arrow f5 marking the exposure to toluene and the arrow f6 marking that of ethanol.

The decreases in the vibration frequency recorded during exposures to organic compound vapours were the following:
DNTFMB $1^{st}$ exposure: −179 Hz
DNTFMB $2^{nd}$ exposure: −139 Hz
Dichloromethane: −291 Hz
Methyl ethyl ketone: −293 Hz
Toluene: −275 Hz
Ethanol: −20 Hz.

EXAMPLE 3

Detection of Two Nitro Compounds (DNT and DNB) by a Third Quartz Microbalance Sensor In this example, a quartz microbalance sensor was used that comprised an identical quartz to that of the sensor used in Example 1 and of which the quartz was covered on both of its faces with a thin film of the bisporphyrin of particular formula (IIIa) represented above.

This film was also deposited by sublimation of said bisporphyrin at a temperature of 100° C., but under a partial vacuum of $2\times10^{-5}$ bar, until a 20 kHz change in the quartz vibration frequency was obtained.

The sensor was exposed successively to:
air for 15 minutes;
DNT at a concentration of 285 ppb in air for 10 minutes;
air for 11 minutes;
DNB at a concentration of 5 ppm in air for 10 minutes; and
air for 20 minutes,
the air, DNT and DNB being at room temperature (25° C.).

Figure 3:
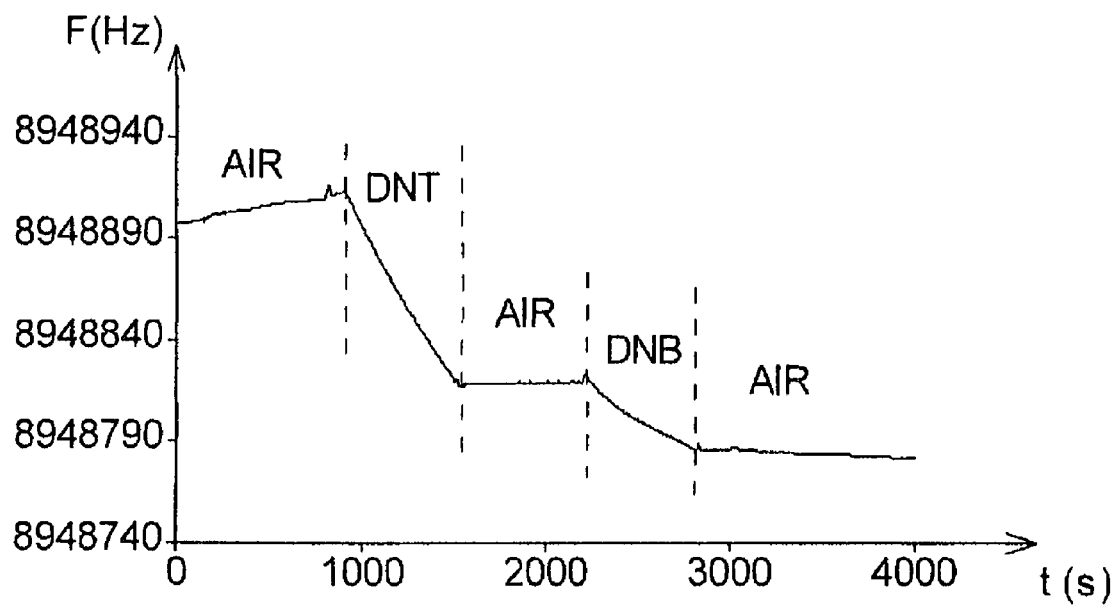
FIG. 3 shows the variation of the quartz vibration frequency of a quartz microbalance sensor comprising a thin film of the first example of a compound used according to the invention, when this sensor is exposed successively to air and to vapours of 2,4-dinitrotoluene (DNT) and of dinitrobenzene (DNB).

FIG. 3 illustrates the change in the quartz vibration frequency during these exposures, in the form of a curve representing the vibration frequency (F) of the quartz, expressed in hertz (Hz), as a function of time (t), expressed in seconds (s).

EXAMPLE 4

Detection of Three Nitro Compounds (TNB, TNT and TATB) by a Quartz Microbalance Sensor In this example, an identical sensor to that used in Example 3 was used.

This sensor was exposed successively to:
air for 15 minutes;
TNB at a concentration of 285 ppb in air for 10 minutes;
air for 8 minutes;
TNT at a concentration of 7 ppb in air for 12 minutes;
air for 36 minutes;
TATB at a concentration below 1 ppt in air for 10 minutes; and
air for 25 minutes, the air, TNB, TNT and TATB being at room temperature (25° C.)

Figure 4:
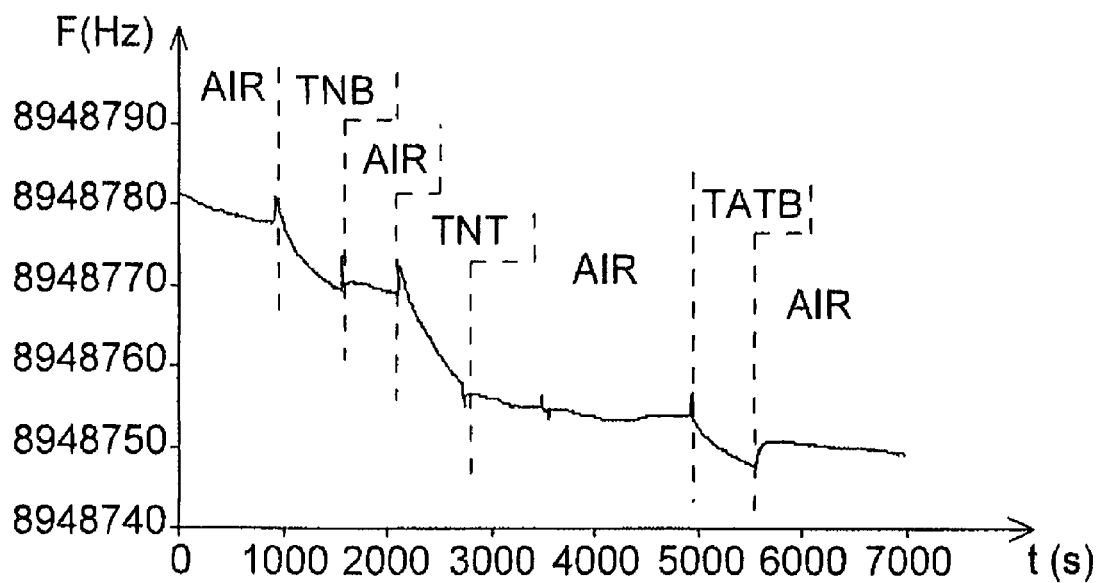
FIG. 4 shows the variation in the quartz vibration frequency of a quartz microbalance sensor comprising a thin film of the first example of a compound used according to the invention, when this sensor is exposed excessively to air and to vapours of trinitrobenzene (TNB), trinitrotoluene (TNT) and triaminotrinitrobenzene (TATB).

FIG. 4 illustrates the variation of the quartz vibration frequency during these exposures, in the form of a curve representing the vibration frequency (F) of the quartz, expressed in hertz (Hz), as a function of time (t), expressed in seconds (s).

EXAMPLE 5

Detection of one Nitro Compound (DNTFMB) by a Quartz Microbalance Sensor

In this example, a quartz microbalance sensor was used that comprised a quartz identical to that of the sensor used in Example 1, but of which the quartz was covered on both of its faces with a thin film of the bisporphyrin of particular formula (IIIc) represented above.

This film was deposited by sublimation of the bisporphyrin, at a temperature of 100° C. and under a partial vacuum of $2\times10^{-5}$ bar, until a 10 kHz change in the vibration frequency of the quartz was obtained.

This sensor was exposed successively to:
air for 25 minutes;
DNTFMB at a concentration of 3 ppm in air for 10 minutes; and
air for 30 minutes, the air and DNTFMB being at room temperature (25° C.).

Figure 5:
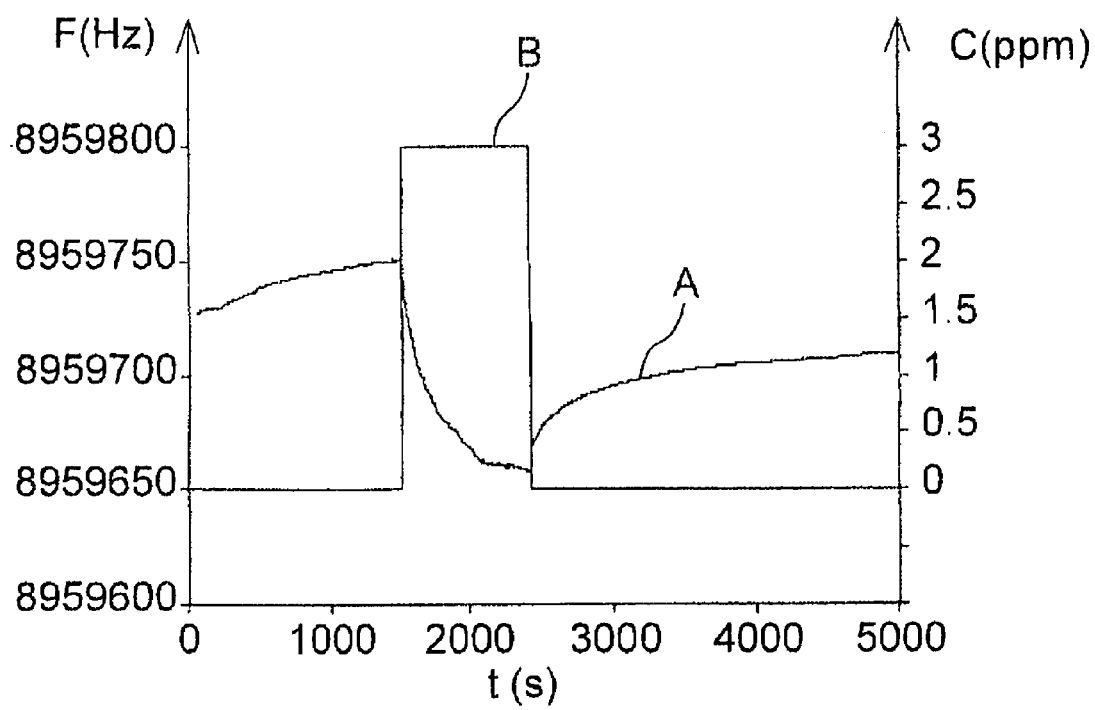
FIG. 5 shows the variation of the quartz vibration frequency of a quartz microbalance sensor comprising a thin film of a third example of a compound used according to the invention, when this sensor is exposed successively to air and to DNTFMB vapours.

FIG. 5 illustrates the variation of the quartz vibration frequency during these exposures. In this figure, the curve A represents the vibration frequency (F) of the quartz, expressed in hertz (Hz), as a function of time (t), expressed in seconds (s), while the curve B represents the concentration of DNTFMB (C), expressed in ppm, also as a function of time.

EXAMPLE 6

Detection of One Nitro Compound (DNTFMB) by a Quartz Microbalance Sensor

In this example, a quartz microbalance sensor was used that comprised a quartz identical to that of the sensor used in Example 1, but of which the quartz was covered on both of its faces with a thin film of the bispolyazamacrocycle of particular formula (IVa) represented above.

This film was deposited on each face of the quartz by spraying a solution of bispolyazamacrocycle in methanol having a concentration equal to 5 g/l sixty times, each lasting 0.4 seconds, so as to obtain a change in the quartz vibration frequency of 10 kHz.

This sensor was exposed successively to:
air for 18 minutes;
DNTFMB at a concentration of 3 ppm in air for 10 minutes; and
air for 20 minutes, the air and DNTFMB being at room temperature (25° C.).

Figure 6:
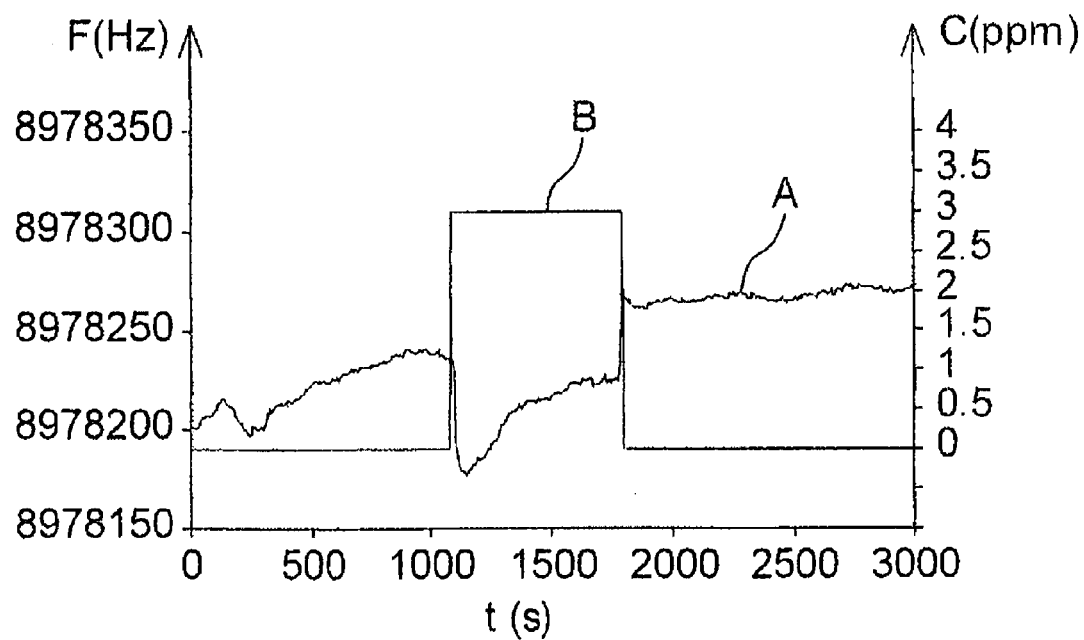
FIG. 6 shows the variation of the quartz vibration frequency of a quartz microbalance sensor comprising a thin film of a fourth example of a compound used according to the invention, when this sensor is exposed successively to air and to DNTFMB vapours.

FIG. 6 illustrates the change in the quartz vibration frequency during these exposures. In this figure, the curve A represents the vibration frequency (F) of the quartz, expressed in hertz (Hz), as a function of time (t), expressed in seconds (s), while the curve B represents the concentration of DNTFMB (C), expressed in ppm, also as a function of time.

EXAMPLE 7

Detection of One Nitro Compound (DNTFMB) by a Fluorescence Sensor

In this example, a sensor was used whose operation was based on the change in the fluorescence intensity emitted by the sensitive material that this sensor comprised in the presence of a nitro compound.

In this particular case, the sensitive material was composed of the dioxomacrocycle of particular formula (VIa) represented above, in the form of a thin film that covered one of the faces of a substrate made of optical quality glass (TUET and BIECHELIN), obtained by spraying a solution of this compound in methanol, having a concentration equal to 5 g/l, fourteen times, each lasting 0.4 seconds.

The thin film thus obtained had a fluorescence intensity of $30 \times 10^5$ cps (counts per second) ($\lambda_{emission}$:511 nm; $\lambda_{excitation}$: 392 nm) as measured using a FluoroMax-3 fluorometer from Jobin Yvon, under dynamic conditions in a cell flushed at 24 l/h and thermostated at 25° C.

The sensor was exposed successively to:
pure nitrogen for 35 minutes;
DNTFMB at a concentration of 1 ppm in nitrogen for 10 minutes;
air for 48 minutes;
DNTFMB at a concentration of 1 ppm in nitrogen for 10 minutes;
air for 120 minutes;
DNTFMB at a concentration of 0.1 ppm in nitrogen for 10 minutes; and
air for 18 minutes, the nitrogen, DNTFMB and air being at room temperature (25° C.).

Figure 7:
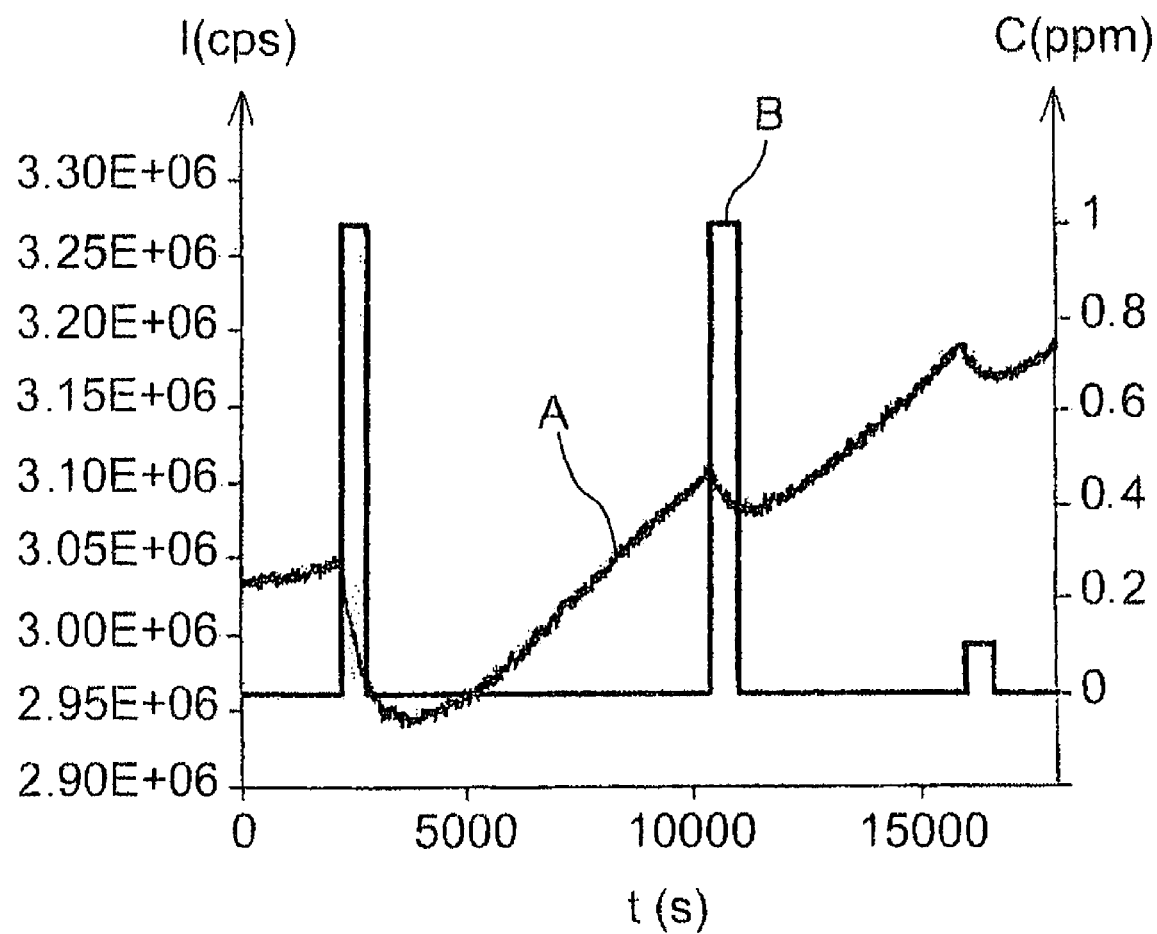
FIG. 7 shows the variation of the fluorescence intensity emitted by a fluorescence sensor comprising a thin film of a fifth example of a compound used according to the invention, when this sensor is exposed successively to air and to DNTFMB vapours.

FIG. 7 illustrates the change in the fluorescence intensity emitted by the sensor during these exposures, this fluorescence intensity being measured under the same conditions as those specified above. In this figure, the curve A represents the fluorescence intensity (I), expressed in counts per second (cps), as a function of time (t), expressed in seconds (s), while the curve B represents the concentration of DNTFMB (C), expressed in ppm, also as a function of time.

The above examples show that quartz microbalance sensors or fluorescence sensors comprising a compound of general formula (I) as sensitive material, are capable of detecting with a very high sensitivity, not only vapours of nitro compounds such as DNTFMB, DNB, TNB, TNT or TATB vapours, but also vapours of other volatile organic compounds such as, for example, those conventionally used as solvents: chlorinated compounds, aromatics, ketones and alcohols. The detection of organic compounds belonging to various classes is thus possible with these sensors.

The examples also show that the response of these sensors is both reversible and reproducible.

The invention claimed is:
1. Process of detecting or assaying one or more organic compounds in the vapour state, the process comprising
contacting one or more organic compounds in the vapour state with a chemical sensor comprising at least one compound corresponding to the general formula (I) below:

wherein:
$MC_1$ and $MC_2$, which may be identical or different, represent macrocycles;
p and q, which may be identical or different, are equal to 0 or 1;
X and Y, which may be identical or different, are optionally substituted alkylene groups comprising from 1 to 10 carbon atoms; while
E represents an optionally substituted cyclic or heterocyclic spacer group; and wherein $MC_1$ and $MC_2$ are positioned facing each other; and
detecting or assaying the one or more organic compounds in the vapour state with the at least one compound corresponding to the general formula (I).

2. The process of claim 1, wherein the macrocycles $MC_1$ and $MC_2$ are molecules that are composed of a single ring or of several rings joined together by a simple bond or via a bridging atom or group, and wherein the ring or the set of rings comprises from 8 to 60 carbon atoms and one or more heteroatoms.

3. The process of claim 2, wherein the macrocycles $MC_1$ and $MC_2$ are chosen from metalled and non-metalled, substituted and unsubstituted porphyrins, phthalocyanins, naphthalocyanins, sapphyrins, corroles, corrolazines and macrocyclic polyamines.

4. The process of claim 3, wherein the metalled porphyrins, phthalocyanins, naphthalocyanins, sapphyrins, corroles, corrolazines and macrocyclic polyamines contain lithium, magnesium, iron, cobalt, zinc, copper, nickel, manganese, chromium, titanium or lead.

5. The process of claim 1, wherein the spacer group E is chosen from phenyl, pyrenyl, anthracenyl, naphthalenyl, dibenzofuranyl, biphenylenyl, dibenzothiophenyl, xanthenyl, metallocenyl, ortho-, meta- or para-xylenyl, carbazolyl, acridinyl, phenazinyl, phenoxazinyl, binaphthyl, phenothiazinyl, fluorenyl, diphenyl ether oxide and calix arenyl groups where n is an integer ranging from 4 to 12.

6. The process of claim 1, wherein:
$MC_1$ and $MC_2$ are identical or different, and represent two porphyrins or two phthalocyanins or two naphthalocyanins or two sapphyrins or two corroles or two corrolazines or two macrocyclic polyamines, each of which are metalled or non-metalled, substituted or unsubstituted;
p and q are identical, X and Y are identical; and E represents an optionally substituted cyclic or heterocyclic spacer group.

7. The process of claim 6, wherein the compound corresponds to the general formula (I) wherein:

MC$_1$ and MC$_2$ represent:

either two porphyrins chosen from those corresponding to formulae (II) and (III):

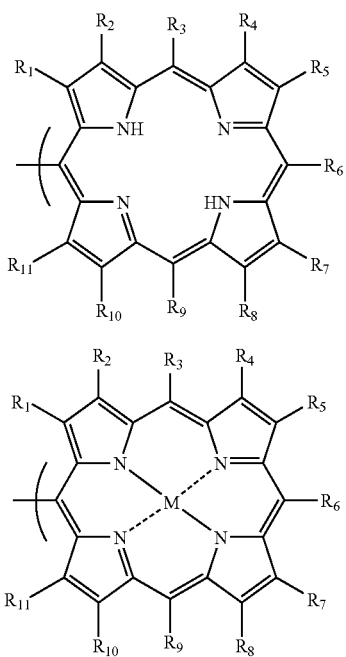

or two dioxopolyazamacrocycles chosen from those corresponding to formulae (IV) and (V):

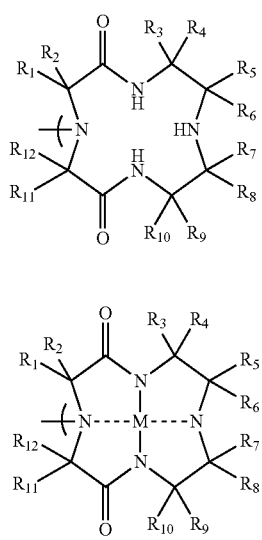

or two polyazamacrocycles chosen from those corresponding to formulae (VI) and (VII):

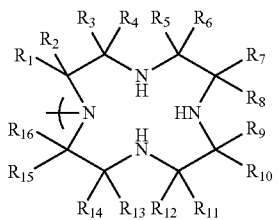

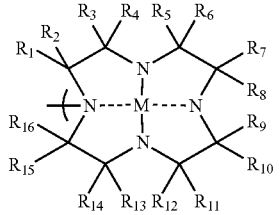

where $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$ and $R^{17}$, being identical or different, represent a hydrogen atom or a linear or branched, saturated or unsaturated, $C_1$ to $C_{10}$ hydrocarbon group and M represents a metal chosen from lithium, magnesium, iron, cobalt, zinc, copper, nickel, manganese, chromium, titanium and lead;

p and q are identical, X and Y are identical; E represents an optionally substituted cyclic or heterocyclic spacer group.

8. The process of claim 1, wherein the compound corresponds to any one of the formulae (IIIa), (IIIb), (IIIc), (IVa,) and (VIa):

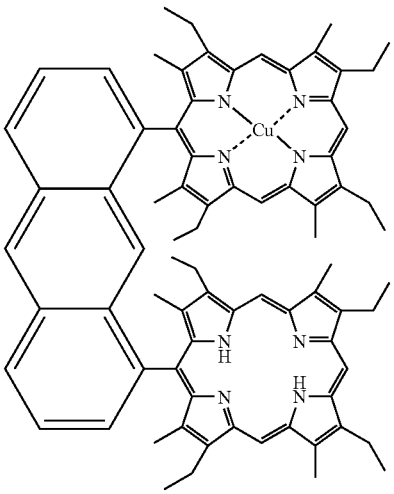

(IIIb)

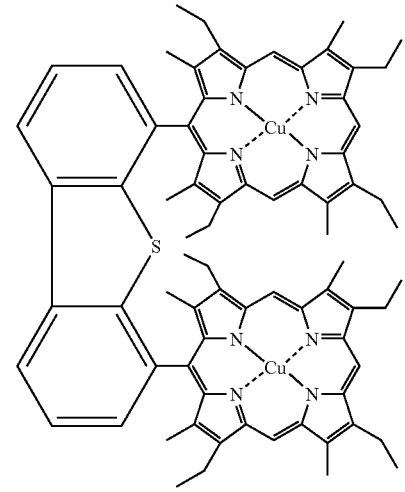

(IIIc)

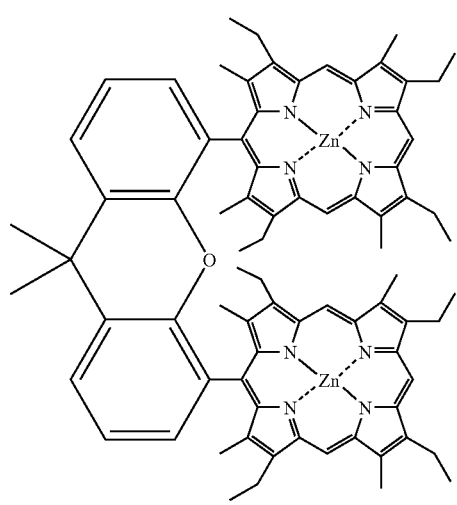

(IVa)

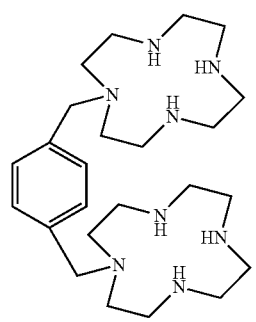

(VIa)

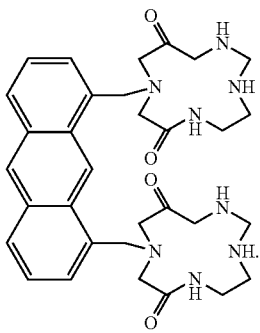

9. The process of claim 1, wherein the compound is present in the chemical sensor in the form of a thin film covering one or both sides of a substrate.

10. The process of claim 9, wherein the thin film measures from 10 angströms to 100 microns in thickness.

11. The process of claim 9, wherein the chemical sensor is a gravimetric sensor.

12. The process of claim 11, wherein the gravimetric sensor is a quartz microbalance sensor.

13. The process of claim 1, wherein the chemical sensor is a fluorescence sensor.

14. The process of claim 1, wherein the chemical sensor is a multisensor comprising one or more gravimetric sensors and/or one or more fluorescence sensors, at least one of these sensors comprising the compound corresponding to the general formula (I).

15. The process of claim 1, wherein the organic compound or compounds to be detected or assayed are one or more nitro compounds.

16. The process of claim 15, wherein the nitro compound or compounds are chosen from nitroaromatic compounds, nitraamines, nitrosamines and nitric esters.

17. The process of claim 16, wherein the nitro compound or compounds are chosen from nitrobenzene, dinitrobenzene, trinitrobenzene, nitrotoluene, dinitrotoluene, trinitrotoluene, dinitrofluorobenzene, dinitrotrifluoromethoxybenzene, aminodinitrotoluene, dinitrotrifluoromethylbenzene, chlorodinitrotrifluoromethylbenzene, hexanitrostilbene, trinitrophenol, cyclotetramethylenetetranitramine, cyclotrimethylenetrinitramine, trinitrophenylmethylnitramine, nitrosodimethylamine, pentrite, ethylene glycol dinitrate, diethylene glycol dinitrate, nitroglycerine or nitroguanidine.

18. The process of claim 1, wherein the sensor detects explosives.

19. The process of claim 1, wherein the organic compound or compounds to be detected or assayed are one or more volatile organic compounds.

20. The process of claim 19, wherein the volatile organic compound or compounds are chosen from ketones, alcohols, chlorinated solvents and aromatic compounds.

* * * * *